United States Patent [19]

Bradfute et al.

[11] Patent Number: 5,567,729
[45] Date of Patent: Oct. 22, 1996

[54] FARNESYL COMPOUNDS AS FARNESYL PROTEIN TRANSFERASE INHIBITORS TO TREAT RAS INDUCED TUMOR GROWTH

[75] Inventors: David L. Bradfute; Robert D. Simoni; Thomas E. Meigs, all of Department of Biological Sciences, Stanford, Calif. 94305

[73] Assignees: David L. Bradfute, Wooster, Ohio; Thomas E. Meigs, Palo Alto; Robert D. Simoni, Stanford, both of Calif.

[21] Appl. No.: 144,700

[22] Filed: Oct. 28, 1993

[51] Int. Cl.$^6$ ............................ A61K 31/22; A61K 31/08
[52] U.S. Cl. ............................................. 514/546; 514/722
[58] Field of Search ..................................... 514/546, 722

[56] References Cited

U.S. PATENT DOCUMENTS 5,185,248  2/1993  Barbacid et al. ......................... 435/15

OTHER PUBLICATIONS

Cox and Der, (1992) Current Opinions in Cell Biology 4:1008–1016. Protein Prenylation: more than just glue?.
G. James, et al. (1993) Science 260:1937–1942. Benzodiazopine peptidomimetics: potent inhibitors of ras farnesylation in animal cells.
N. Kohl, et al. (1993) Science 260:1934–1936. Selective inhibition of ras–dependent transformation by a farnesyltransferase inhibitor.
J. Gibbs, et al. (1993) Journal of Biological Chemistry 268:7617–7620. Selective inhibition of farnesyl–protein transferase blocks ras processing in vivo.
DeClue, et al. (1991) Cancer Research 51:712–717. Inhibition of cell growth by lovastatin is independent of ras function.
D. Pompliano, et al. (1992) Biochemistry 31:3800–3807. Steady–state kinetic mechanism of ras farnesyl:protein transferase.
Der and Cox (1991) Cancer Cells 3:331. Isoprenoid modification and plasma membrane association: critical factors for ras oncogenicity.
Cox, et al. (1992) Molecular and Cellular Biology 12:2606–2615. Specific isoprenoid modification is required for function of normal, but not oncogenic, ras protein.
Kato, et al. (1992) P.N.A.S. 89:6403–6407. Isporenoid addition to ras protein is the critical modification for its membrane association and transforming activity.
Sinensky and Lutz (1992) BioEssays 14:25–31. The prenylation of proteins.

*Primary Examiner*—Jerome D. Goldberg
*Attorney, Agent, or Firm*—Bertram I. Rowland; Pamela J. Sherwood

[57] ABSTRACT

Farnesyl derivatives, particularly farnesyl acetate, are used to reduce the level of protein farnesylation in a mammalian host. The activity of proteins which require farnesylation for function is thereby reduced. The compounds may be administered to patients to reduce the overall level of ras protein activity, either alone or in conjunction with other drugs which act as competitive inhibitors of farnesyl protein transferase.

7 Claims, No Drawings

FARNESYL COMPOUNDS AS FARNESYL PROTEIN TRANSFERASE INHIBITORS TO TREAT RAS INDUCED TUMOR GROWTH

This invention was made with Government support under contract 5R01HL26502 awarded by the National Institutes of Health. The Government has certain rights in this invention.

TECHNICAL FIELD

The field of this invention is the reduction in the level of protein farnesylation in a mammalian host.

BACKGROUND

In recent years it has been shown that in eukaryotic cells, proteins may be modified by the addition of isoprenoid groups to the amino acid backbone. The isoprenoid groups, in particular farnesyl and geranylgeranyl, are attached at the carboxy terminus of the protein, by a thioether linkage to a terminal cysteine residue.

Proteins which are modified in this way have increased affinity for specific membranes and certain integral membrane proteins. The addition of a prenyl group increases hydrophobicity. The hydrophobicity is further increased by cleavage of the three amino acids C-terminal to the cysteine, and by methylation of the now terminal cysteine.

The addition of prenyl groups may be required for activity of the protein. In the ras family of proteins, addition of a farnesyl group is required for normal activity. A mutated form of ras, which can be modified by the addition of geranylgeranyl, has transforming activity but not normal function. Blocking all prenylation results in a soluble protein which is not active.

Specific enzymes have been shown to catalyze the addition of farnesyl and geranylgeranyl groups. A consensus sequence for a protein to be prenylated is the "CAAX" box, where C is cysteine, A is an aliphatic amino acid, and X may be any amino acid. The amino acid "X" determines whether the protein will be modified with farnesyl or geranylgeranyl. A CC or CXC carboxy terminal peptide motif can also signal for the addition of geranylgeranyl. Most prenylated proteins are geranylgeranylated, and a minority are modified with farnesyl groups. Proteins which are modified by farnesylation include ras, lamins and the γ subunit of transducin.

There are at least two proteins which are active in transferring geranylgeranyl groups to proteins. However, there is only one enzyme in mammals which is active in transferring farnesyl to proteins, farnesyl protein transferase (FPTase). The protein, which has recently been cloned, is an α, β heterodimer. The protein substrate binds to the β subunit, while the α subunit binds farnesyl diphosphate. The biological activity of farnesylated proteins makes it of interest to determine whether farnesyl protein transferase activity can be reduced.

RELEVANT LITERATURE

A review of protein prenylation, and its role in protein function, is provided in Cox and Der, (1992) Current Opinions in Cell Biology 4:1008–1016, and in Sinensky and Lutz (1992) BioEssays 14:25–31.

Der and Cox (1991) Cancer Cells 3:331 review the role of isoprenoid modifications in ras protein oncogenicily. Cox, et al. (1992) Molecular and Cellular Biology 12:2606–2615 describe the role of specific isoprenoid groups in ras function, specifically the effects of geranylgeranyl vs. farnesyl groups. Karo, et al. (1992) P.N.A.S. 89:6403–6407 show that isoprenoid addition to ras protein is the critical modification for its membrane association and transforming activity.

Farnesyl diphosphate analogs as inhibitors of farnesyl protein transferase are discussed in DeClue, et al. (1991) Cancer Research 51:712–717, showing that inhibition of cell growth by lovastatin is independent of ras function. A method of assaying for farnesyl protein transferase activity is described in U.S. Pat. No. 5,185,248. D. Pompliano, et al. (1992) Biochemistry 31:3800–3807 describes steady-state kinetic mechanisms of ras farnesyl:protein transferase, and shows that two non-hydrolyzable analogues of farnesyl diphosphate, (α-hydroxyfarnesyl)phosphonic acid and [[(farnesylmethyl)hydroxyphosphinyl]methyl]phosphonic acid compete with farnesyl diphosphate for binding to farnesyl protein transferase. J. Gibbs, et al. (1993) Journal of Biological Chemistry 268:7617–7620 discusses selective inhibition of farnesyl protein transferase, where three structural classes of competitive inhibitors of farnesyl protein transferase were identified: (α-hydroxyfarnesyl)phosphonic acid, chaetomellic acid, and zaragozic acid. Ras processing was inhibited by (α-hydroxyfarnesyl)-phosphonic acid, but not by chaetomellic acid or zaragozic acid in vivo.

The use of CAAX box analogs to block farnesylation is discussed in N. Kohl, et al. (1993) Science 260:1934–1936. The results demonstrate selective inhibition of ras-dependent cell transformation with a synthetic organic inhibitor of FPTase, L-731,734 tetrapeptide analog. G. James, et al. (1993) Science 260:1937–1942 shows benzodiazopine peptidomimetics as potent inhibitors of ras farnesylation in animal cells. Replacement of two aliphatic residues of the tetrapeptide with a benzodiazopine-based mimic generated inhibitors of farnesyltransferase.

SUMMARY OF THE INVENTION

Methods are provided to reduce the level of protein farnesylation in a mammalian host by administration of farnesyl derivatives, particularly farnesyl acetate. The enzyme responsible for the transfer of farnesyl groups to proteins, farnesyl protein transferase, is inhibited by the presence of farnesyl compounds of the formula:

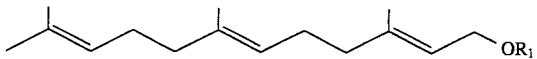

where $R_1$ may be a lower alkyl, or an acyl group

where $R_2$ may be any lower alkyl. The farnesyl compounds are analogs of farnesyl diphosphate, and act as competitive inhibitors for the α subunit of FPTase. The activity of proteins which require farnesylation for function is thereby reduced.

DESCRIPTION OF THE SPECIFIC EMBODIMENTS

Methods are provided to reduce protein farnesylation in cells. Farnesyl esters and ethers are analogs of farnesyl diphosphate (FPTase), and act as competitive inhibitors for the α subunit of FPTase. The compounds may be administered to patients with ras associated tumors in order to decrease the tumor growth.

The farnesyl compounds are characterized by the formula

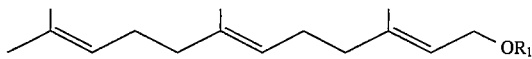

where $R_1$ may be a lower alkyl, or an acyl group

where $R_2$ may be any lower alkyl, wherein lower alkyl is of from 1 to 6 carbon atoms, particularly 1 to 4 carbon atoms, more particularly methyl, ethyl and propyl. The farnesyl compounds, particularly farnesyl acetate, decrease activity of FPTase, and block protein farnesylation.

The compounds are administered to patients with tumors which are associated with abnormal activity of oncogenes in the ras family, in which the protein products are known to require prenylation for activity. Proteins of the ras family include the three mammalian ras genes, H-ras, K-ras and N-ras. Other ras proteins include those whose DNA coding regions will hybridize under stringent conditions to the coding region of known ras genes. Ras proteins are members of a superfamily of low molecular weight (20–25 kD) GTP-binding proteins. Abnormal ras activity is associated with 30–50% of all lung and colorectal carcinomas, and up to 95% of pancreatic carcinomas.

The compounds are administered in a dosage from 5 mg to 1400 mg, more usually from 100 mg to 1000 mg, preferably 500 to 700 for a dose of 0.5 to 20 mg/kg weight. The dosage is selected so that the activity of farnesyl protein transferase is reduced by 40 to 80% and specifically, the growth of ras associated tumor cells is reduced.

Patients are treated with a therapy comprising administration of said farnesyl compounds, for the most part, farnesyl acetate. The compounds may be administered in a variety of ways, orally, parenterally, etc. For injection, the farnesyl compounds may be injected subcutaneously, intraperitoneally, intravascularly, etc. Depending upon the manner of introduction, the compounds may be formulated in a variety of ways. The concentration of therapeutically active compound in the formulation may vary from about 0.5–100 wt. %.

The pharmaceutical compositions can be prepared in various forms, such as granules, tablets, pills, suppositories, capsules, suspensions, salves, lotions and the like. Pharmaceutical grade organic or inorganic carders and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

For oral application, the pharmaceutical composition will generally contain from about 5–100% by weight of the active material. For other applications, the composition will generally have from about 0.5–50 wt. % of the active material. Various carders include excipients, sugars, alum, dimethyl sulfoxide, etc.

The subject compositions will generally be administered daily. Generally, the total daily dosage will be at least about 10 mg, usually at least about 400 mg to 500 mg, preferably about 700 mg, and not more than about 1500 mg, usually not more than about 1000 mg. The amount may vary with the general health of the patient, the response of the patient to the drug, whether the farnesyl compound is used by itself or in combination with other drugs, and the like. Daily administrations may be one or more times, usually not more than about four times, particularly depending upon the level of drug which is administered.

Of particular interest is the use of other agents, particularly those which act as competitive inhibitors for the β subunit of FPTase, in combination with the subject compounds. By inhibition of both the α and β subunit of FPTase, a more complete block of activity may be achieved, allowing the use of lower dosages of each drug. Examples of such agents include those which are analogs of the tetrapeptide CAAX box. The tetrapeptide analog prodrug L-731,734 (N. Kohl, et al. (1993) Science 260: 1934) and benzodiazopine derivatives of the tetrapeptide CVFM (G. James, et al. (1993) Science 260:1937) are competitive inhibitors of the β ubunit of FPTase for the protein substrate, and may be used in combination therapy with the subject compounds.

The following examples are offered by way of illustration and not by way of limitation.

EXPERIMENTAL

Example I

Inhibition of Protein Farnesylation by Farnesyl Acetate and Farnesyl Ethyl Ether Methods Met-HMGal cells, which are hamster 18b cells stably transfected with a plasmid encoding the chimeric protein HMGal were used for these experiments. The cells were grown as amonolayer in mimum essential medium (MEM) supplemented with 5% fetal calf serum and 0.25 mg/ml active geneticin. For each experiment, cells were grown in 6 cm dishes to approximately 75% confluency, then washed twice with phosphate buffered saline (PBS). Each dish then received 1 ml of MEM supplemented with 5% lipidfree serum and 50 µM compactin. After 75 minutes, dishes received either farnesyl acetate at 10, 20 and 40 µg/ml, or farnesyl ethyl ether at 5, 10 and 20 µg/ml, or no addition. After 1 h, each dish received 100 µCi of RS-[5-$^3$H(N)] menalonolactone (NEN Research Products) and the dishes were incubated an additional 5 h. In a second experiment, the protocol was altered by adding the radiolabel simultaneously with the farnesyl compounds, and the dishes were then incubated for 2 h. Next, each dish was washed twice with cold PBS and cells were solubilized with 150 gl lysis buffer (PBS, 1% deoxycholate, 1% Nonidet P-40, 5 mM EDTA, 5 mM EGTA, 2 mM phenylmethylsulfonyl fluoride, 0.1 mM leupeptin, 2 µg/ml calpain inhibitor I). Lysates were centrifuged 30 min at 16000×g, and supernatants were collected. A 30 µl aliquot was taken from each sample and protein was done by the method of Lowry, et al. The appropriate amount from each sample was then mixed with loading buffer containing 25 mg/ml dithiothrietol, and incubated at 80° for 20 min, then electrophoresed by SDS-PAGE on an 8–16% gradient gel for 16 h. The gel was impregnated with fluorgraphic enhancer, then dried under vacuum and allowed to expose X-ray film at −80° for 3–5 days. Visible bands of farnesylated and geranylgeranylated proteins were distinguished, then quantified by densitometry.

Results:

Farnesylation was effectively hindered by the presence of farnesyl acetate at concentrations of 10 and 20 µg/ml. Based on two separate experiments, 10 µg/ml farnesyl acetate caused a 36–57% loss of farnesylation in cellular proteins, while geranylgeranylation was reduced by 10–32%. At 20

μg/ml farnesyl acetate caused a 64–79% loss of farnesylation in cellular proteins, while geranylgeranylation was reduced by 43–47%. At 40 μg/ml, farnesyl acetate appeared to be toxic to the cells. Farnesyl ethyl ether also blocked farnesylation to a greater degree than geranylgeranylation, but it was less effective than farnesyl acetate.

Example II

Inhibition of Protein Farnesylation by Farnesyl Acetate in Vitro

A reaction is set up according to the protocol of Miura, et al. (1993) FEBS Letters 318:88–90. Briefly, a reaction system is assembled using 0.2 μM [$^3$H] farnesyl pyrophospate, 35 μg/ml farnesyl transferase, and 3.4 μM of a synthetic substrate for farnesyl transferase, N-lys-thr-ser-cys-val-ile-met-C. The reaction is buffered with 50 mM potassium phosphate, pH 6.5, 0.2 mM zinc chloride, 4 mM magnesium chloride, 50 mM potassium chloride and 1 mM dithiotrietol. This system is incubated in the presence of 10, 20 and 40 μg/ml of farnesyl acetate or farnesyl ethyl ether. At 10 minute intervals, a small amount of each sample is spotted onto a silica gel plate, and spots are counted for radioactivity to quantify the incorporation of radioactivity onto the heptapeptide for each sample. Following treatment with farnesyl acetate, inhibition of incorporation of radioactivity onto the heptapeptide is observed.

Example III

Inhibition of Ras Farnesylation by Farnesyl Acetate

Metabolic Labeling and Immunoprecipitation of Ras Proteins

Cells are plated at a density of $2 \times 10^6/75$ cm$^2$ flask. Labeling with [$^{35}$S]methionine is carded out in 2 ml of methionine-free DMEM supplemented with 10% regular DMEM; 2% fetal bovine serum, and 200 μCi/ml 35S-Translabel. Labeling with [$^{14}$C]farnesyl pyrophosphate is carded out in regular medium with 10% fetal bovine serum for 6 h with 2 mCi/ml. For the labeling experiments, farnesyl acetate treatment is for 24 h prior to cell lysis, inclusing the labeling period.

Cells are lysed as described in Papageorge, et al (1982) J. Virol. 44:509–519. For analysis of [$^{35}$S]-labeled cells, lysates containing equal numbers of acid-precipitable counts are analyzed. The entire lysate from one flask is analyzed for the [$^3$H]-labeled cells. Lysates are immunoprecipitated with the ras specific monoclonal antibody Y13-259. Following a 2 h antibody incubation, 60 μl of a 10% suspension of protein A-sepharose coated with rabbit-anti rat IgG are added for 45 min. The immunoprecipitates are washed 4 times with wash buffer, boiled in SDS sample buffer, and loaded on 15% polyacrylamide gels.

Example IV

Effect of Farnesyl Acetate on Growth of Transformed Cell Lines

Derivation and Culture of Cell Lines

Morphological transformation is induced by calcium phosphate transfection of the NIH 3T3 line with the following plasmids: pBW1423 for v-ras$^H$; pBW163 1 for c-ras$^H$; pJDC1 for v-src; and MSV3611 proviral DNA for v-raf.

With the exception of the v-raf plasmid, each of the above plasmids contains neo as a linked selectable marker. All cell lines except the v-raf are generated by selection with G418 (600 μM) for 10–14 days, isolation of individual transformed colonies with cloning cylinders, and expansion into cell lines. The v-raf line is generated by cloning an individual focus of transformed cells and expansion into a cell line. Cells are cultured in DMEM supplemented with 10% fetal bovine serum and 600 μM G418 where required.

Growth Inhibition Assays

On day 0, cells are trypsinized and plated at 10$^4$/well in 8 triplicate sets in 24 well plates. On day 3, cells are fed with fresh medium containing either 0, 5, 10, or 15 μM farnesyl acetate. After 48 h, one triplicate set of each concentration is trypsinized and counted in a Coulter Counter. The other triplicate sets are fed fresh medium with or without farnesyl acetate at this time. Two days later, the other triplicate sets are trypsinized and counted.

The parental NIH 3T3 cell line exhibits a flat, non-refractile morphology, with fully contact-inhibited growth. In contrast the raf transformed cells have an elongated, refractile appearance, and tend to pile on top of each other. Cells transformed with src have a more rounded appearance, while ras transformed lines are somewhere between the two. All of the transformed cells tend to pile on top of each other. The growth rates of all the transformed cells exceed that of the parental line. Following treatment with farnesyl acetate, inhibition of cell growth and change in morphology is observed.

Example V

Effect of Combined Therapy on Growth of Transformed Cell Lines

Cells are grown as described in Example IV. On day 3, the cells are treated with farnesyl acetate at 0, 5, 10, or 15 μM final concentration and one of the following β subunit inhibitors, at the concentrations listed.

| | |
|---|---|
| L-731,734 | 0.01, 0.1, 1, 10 mM final concentration |
| CVFM tetrapeptide | 0.01, 0.1, 1, 10 mM final concentration |
| BZA-2B (James, et al., supra) | 0.01. 0.1, 1, 10 mM final concentration |
| BZA-4B (James, et al., supra) | 0.01, 0.1, 1, 10 mM final concentration |

The growth and morphology of the cells after treatment is assessed to determine the optimal concentration for a combined therapy.

It is evident from these results that farnesyl acetate is effective in reducing the modification of proteins by farnesylation in a mammalian cell.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for reducing the level of protein farnesylation in mammalian tumor cells in a mammalian host that are associated with abnormal activity of oncogenes in the ras family, wherein said tumor cells are sensitive to treatment with a compound with the formula:

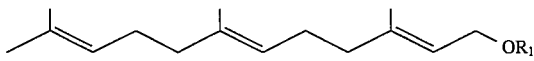

where $R_1$ is a lower alkyl, or an acyl group

and where $R_2$ is any lower alkyl, said method comprising:
- administering to said mammalian host an amount effective to inhibit the activity of farnesyl protein transferase of said compound;
- wherein the activity of farnesyl protein transferase and the growth of said mammalian tumor cells is reduced.

2. A method according to claim 1, wherein said compound is farnesyl acetate.

3. A method according to claim 1, wherein said amount is effective to reduce the activity of farnesyl protein transferase from about 50 to 80%.

4. A method according to claim 1, wherein said protein farnesylation modifies protein substrates characterized by the carboxyl terminal sequence CAA'X, wherein C is cysteine, A is an aliphatic amino acid, A' is an aliphatic but not aromatic amino acid, and X is serine, methionine, cysteine, alanine or glutamine.

5. A method for reducing the proliferation of tumor cells in a patient, said tumor cells being associated with abnormal activity of the protein N-ras, K-ras or H-ras, wherein said tumor cells are sensitive to treatment with a compound with the formula:

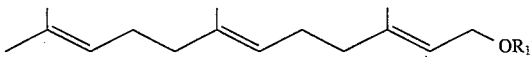

where $R_1$ is a lower alkyl, or an acyl group

and where $R_2$ is any lower alkyl, the method comprising:
- administering to said patient an amount effective to lower the activity of said N-ras, K-ras or H-ras, of said compound
- wherein the proliferation of said tumor cells is reduced.

6. A method according to claim 5, further comprising the step of administering an effective amount of a compound which acts as a competitive inhibitor for the β subunit of farnesyl protein transferase.

7. A method for reducing the level of protein farnesylation in mammalian tumor cells in a mammalian host that are associated with abnormal activity of oncogenes in the ras family, wherein said tumor cells are sensitive to treatment with a compound with the formula:

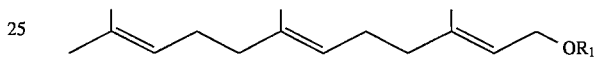

where $R_1$ is an acyl group

and where $R_2$ is any lower alkyl, said method comprising:
- administering to said mammalian host an amount effective to inhibit the activity of farnesyl protein transferase of said compound; and
- wherein the activity of farnesyl protein transferase and the growth of said mammalian tumor cells is reduced.

* * * * *